(12) United States Patent
Tkaczyk et al.

(10) Patent No.: US 7,298,812 B2
(45) Date of Patent: Nov. 20, 2007

(54) IMAGE-BASED MATERIAL DECOMPOSITION

(75) Inventors: J. Eric Tkaczyk, Delanson, NY (US); William Macomber Leue, Albany, NY (US); Walter Irving Garms, Berkeley, CA (US); Joseph Bendahan, San Jose, CA (US); Deborah Walter, Burnt Hills, NY (US); Sussan Pourjavid-Granfors, Sunnyvale, CA (US); Xiaoye Wu, Rexford, NY (US); Peter Michael Edic, Albany, NY (US); Pierfrancesco Landolfi, Newark, CA (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 11/278,287

(22) Filed: Mar. 31, 2006

(65) Prior Publication Data

US 2007/0237288 A1   Oct. 11, 2007

(51) Int. Cl.
*G01N 23/00* (2006.01)

(52) U.S. Cl. .............................. 378/5; 378/4
(58) Field of Classification Search ............... 378/4, 378/5, 16, 15, 19, 901, 8; 382/131; 600/425
See application file for complete search history.

(56) References Cited

U.S. PATENT DOCUMENTS

| 5,661,774 | A | 8/1997 | Gordon et al. | |
| 6,904,118 | B2 * | 6/2005 | Wu et al. | 378/5 |
| 2004/0102688 | A1 * | 5/2004 | Walker et al. | 600/407 |
| 2004/0136491 | A1 * | 7/2004 | Iatrou et al. | 378/4 |
| 2004/0264627 | A1 | 12/2004 | Besson | |
| 2004/0264628 | A1 * | 12/2004 | Besson | 378/5 |
| 2006/0067461 | A1 * | 3/2006 | Yin et al. | 378/5 |

* cited by examiner

*Primary Examiner*—Hoon Song
(74) *Attorney, Agent, or Firm*—William E. Powell, III; Curtis B. Brueske (57) ABSTRACT

A CT scanner acquires CT images at different energy levels and registers those images to provide a composite image that is substantially free of beam hardening artifacts and conspicuously provides atomic information of that imaged.

26 Claims, 6 Drawing Sheets

μ... has units $cm^2/gram$
g... has units $gram/cm^2$

IMAGE-BASED MATERIAL DECOMPOSITION

BACKGROUND OF THE INVENTION

The present invention relates generally to diagnostic imaging and, more particularly, to image-based material decomposition with beam hardening correction.

Helical or axial computed tomography (CT) is an effective imaging modality that presents 2D or volumetric images representative of the x-ray attenuation density of the interior of an object or subject to be imaged. The terms "object" and "subject" are interchangeable and correspond to anything capable of being imaged. The images are reconstructed from sinogram data acquired by scanning the object with an axial or helical protocol. Notwithstanding the numerous advancements in CT imaging, without a priori chemical composition information about the object, the attenuation of x-rays by the object cannot be represented as a line integral across the object thickness. Rather, the attenuation results from a convolution across a broad spectrum of x-ray photon energies delivered by the x-ray source. The lack of a line integral representation results in "beam hardening error" in the sinogram data. Subsequent reconstruction of the sinogram results in beam hardening artifacts in the image.

In addition to the standard attenuation (i.e. Hounsfield unit) images, CT can provide an estimate of atomic number of the interior region of the scanned object. Equivalently, the composition of the interior region can be represented as an equivalent mixture of two basis materials or as a combination of Compton and Photoelectric attenuation parts. Hencefore, reference to atomic number is to any of the equivalent compositional representations possible with dual energy data. These representations of composition have been found to be useful for detection and classification of the object in industrial and medical applications. By processing dual energy sinogram data with a material decomposition algorithm, the beam hardening errors are prevented and accurate atomic number information can be obtained. However, in order to process the data in the sinogram domain, it is necessary to identically register all source-to-detector angles in low and high energy projection views of the sinogram. Lack of such registration results in errors in the material decomposition sinogram. This registration requirement greatly constrains the system architecture and speed at which a given volume of the object can be scanned when using sinogram-based material decomposition. This is particularly true for systems where dual energy data is acquired by separate scans at two different kvp or spectral filter conditions. One proposed system uses a fast kvp switching circuit yielding separate low and high energy images. This system similarly suffers from beam hardening due to misregistered views acquired at different times and view angles. Furthermore, a fast switching circuit will give insufficient control of the x-ray source beam current and kvp for high view rate acquisitions due to the long thermal time constants of the source filament and the electrical time constants of the high voltage system reactance.

Image-based material decomposition has been proposed to extract atomic number information. However, with image-based material decomposition, separate high and low energy images are first reconstructed from sinogram data. A material decomposition algorithm is then applied to the image data. However, the images themselves can suffer from beam-hardening inaccuracies that can lead to errors in the atomic information gathered.

For conventional CT imaging with data at only one tube voltage setting, artifacts are mitigated by performing a beam hardening correction on the sinogram data. The measured $\rho$ value is increasingly suppressed below a linear dependence with respect to the actual $\rho$ value. As is known to those skilled in the art, the $\rho$ value refers to a log-normalized projection value of an x-ray measurement. The $\rho$ value may be used to determine the thickness of a material based on the total x-ray attenuation and incident x-ray measurements. A larger $\rho$ value corresponds to thicker and denser material in the path between the source and detector. As a result of the non-linear transform, a cupping artifact can result in the reconstructed image. The beam hardening effect can be corrected well for the case where the object is composed identically with the assumed material, usually water. By fitting a beam hardening curve to a polynomial and transforming, the measured sinogram multiplicatively with this polynomial transforms to some linear relation. The elimination of cupping in the image is typically accomplished by assuming water to be the material. In the case where the object material is inhomogeneous in composition and not known a priori, this beam hardening correction, using water's parameters, does not completely remove the artifacts in the image. The presence of artifacts in images of inhomogeneous objects will result in error in the atomic number determinations. And, since most objects are inhomogenous, that is, composed of different materials, conventional image-based decomposition can result in artifact-prone images.

When (registered) dual energy sinogram data is available from CT systems, sinogram-based material decomposition is applied to extract atomic number information in a way that is insensitive to beam hardening. Sinogram-based material decomposition self-consistently removes the beam hardening effects in the sinogram and produces chemical composition information for each ray of the sinogram in one algorithmic operation. In order to obtain registered dual kvp sinogram data in a CT system, it is necessary to perform repeated axial mode acquisitions with a motionless object. Volumetric data is built up in such an axial-mode by incrementing the object after acquisition of a complete set of high and low data (step and shoot mode). To acquire aligned sinogram data, each energy acquisition involves at least a full rotation of the gantry so that the low and high energy data can be acquired with identical view angles. This full rotation of 360 degrees is more than required for generation of conventional CT images and can slow the acquisition process. For example, the translation of the object can be delayed until the full 360 degree rotation is complete and overshoot in angle may require waiting for the next rotation in order to insure identically registered views. Furthermore, mechanical inaccuracies can cause the data in the two views not to be coincident. The CT data acquisition process in conventional (non-dual-energy) CT can be accelerated by acquiring data from a scan with only 180 degrees plus detector fan angle. In addition, CT data acquisition can be faster by using more than one detector row (multi-slice CT), or with a helical acquisition with a continuously translated object. However, the registration of x-rays at two energies in these acquisition modes cannot be made identical unless the object is sent through the system twice with careful placement of the object. Alternately, duplicate system hardware can be arrayed along the direction of travel of the object with each system running at one of the two kvp settings. Such duplicative hardware is cost-prohibitive and can result in a prohibitively large scanner.

Computed tomography systems with a dual-source x-ray tube and a wide detector have been suggested to acquire high and low kvp data. In these systems, the x-ray source has two anodes that operate at low and high kvp. This configuration has been shown to result in sinogram misregistration. Moreover, such dual-system architectures are cost intensive solutions to the problem of dual-energy data acquisition and registration. Alternately, systems with energy-sensitive detectors have been proposed, but these systems require a detector architecture that is cost prohibitive.

Therefore, it would be desirable to have a data acquisition process that is efficient and avoids redundant scans as well as an image reconstruction process that includes imaged-based material decomposition to gather atomic number information of an object and that yields an image substantially free of beam hardening artifacts without a substantial increase in scan time.

BRIEF DESCRIPTION OF THE INVENTION

The present invention overcomes the aforementioned drawbacks with a method and apparatus for acquiring CT images at different energy levels and registering those images to provide a composite image that is substantially free of beam hardening artifacts and conspicuously provides composition information of that imaged. In one embodiment, multiple gantry rotations of a helical are segmented into a low energy segments and a high energy segments so that dual-energy data can be acquired in one or more gantry rotations and with a single x-ray source. In the context of this invention, the motion of the gantry relative to the imaged object can be configured to affect a scan in helical or step-and-shoot modes.

In addition to the segmented scan just described, a system with fast kvp switching between each view can also benefit by iterative beam hardening corrections if the registration in the sinogram domain is lacking. In these cases, image domain material decomposition analysis with beam hardening correction is needed to reveal atomic number or material composition information.

Therefore, in accordance with one aspect, the invention includes an imaging apparatus having a data acquisition system configured to reconstruct an image of an object. The apparatus further includes a computer programmed to define a given projection into a first segment and a second segment different from the first segment and acquire a first set of data in the first segment and acquire a second set of data in the second segment. The first set of data is acquired at a first energy level and the second set of data is acquired at a second energy level that is different from the first energy level. The computer is further programmed to reconstruct a first image from the first set of data and a second image from the second set of data, and then automatically register the first and the second images into a composite image substantially free of beam hardening artifacts and that at least provides material decomposition information.

In accordance with another aspect, the invention includes a computer readable storage medium having a computer program stored thereon and representing a set of instructions that when executed by a computer causes the computer to perform image-based atomic number mapping of an object imaged in a dual-energy mode.

According to another aspect, the invention is embodied in a method of CT imaging that includes determining a first attenuation coefficient for a given pixel in a first image and determining a second attenuation coefficient, different from the first attenuation coefficient, for the given pixel in a second image, different from the first image. The method further determines a linear coefficient ratio between the first attenuation coefficient and the second attenuation coefficient and determines an atomic make-up for the given pixel from the linear coefficient ratio. The method further includes the step of displaying a registered image comprised of the first and the second images with the given pixel in the registered image displayed in a conspicuous manner to indicate the atomic make-up of that imaged in the given pixel.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

Figure 1:
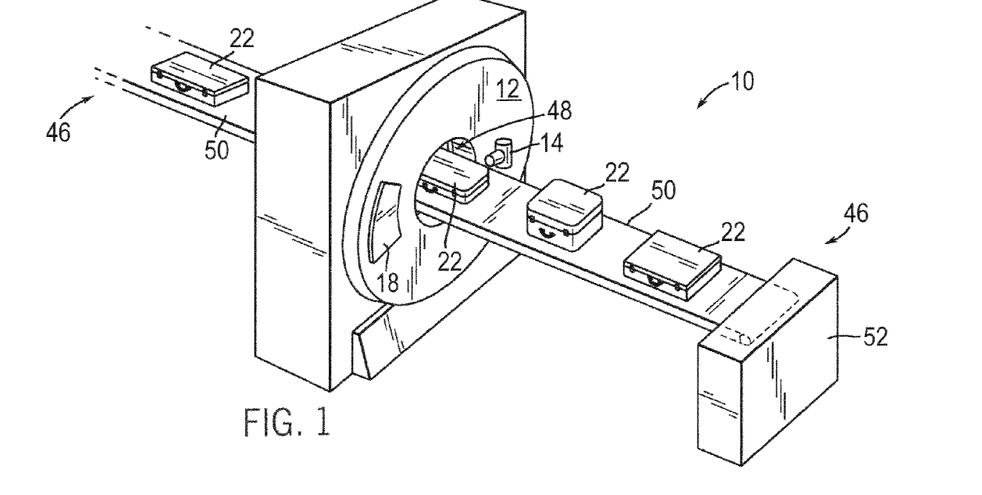
FIG. 1 is a pictorial view of a CT system for use with a non-invasive package inspection system.
Figure 2:
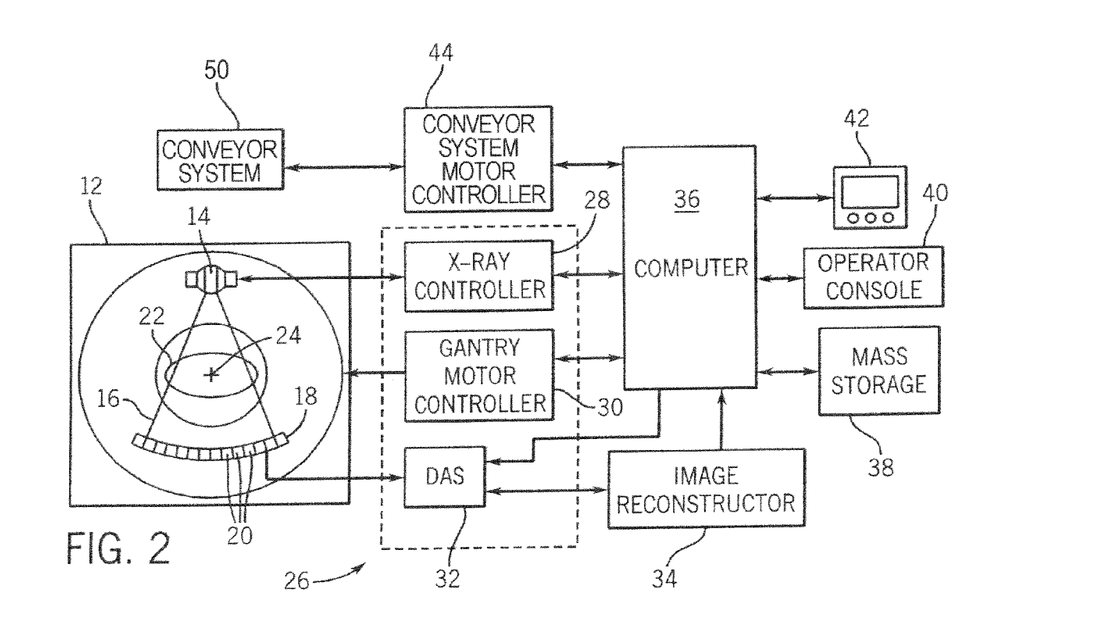
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner for scanning luggage, parcels, and packages. Gantry 12 has an x-ray source 14 that projects a beam of x-rays 16 toward a detector array 18 on the opposite side of the gantry 12. The x-ray source is preferably a single-anode x-ray source. Detector array 18 is formed by a plurality of detectors 20 which together sense the projected x-rays that pass through an object 22. Each detector 20 produces an electrical signal that represents the intensity of an impinging x-ray beam and hence the attenuated beam as it passes through the patient 22. It is contemplated that each detector 20 may be an energy integrating detector or a photon counting energy discriminating detector. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30.

In addition, computer 36 operates a table motor controller 44 which controls a motorized conveyor system 46 to position objects 22 through a gantry opening 48. The conveyor system 46 includes a conveyor belt 50 supported by structure 52 to automatically and continuously pass packages or baggage pieces 22 through opening 48 to be scanned. Objects 22 are fed through opening 48 by conveyor belt 50, imaging data is then acquired, and the conveyor belt 50 removes the packages 22 from opening 48 in a controlled and continuous manner. As a result, postal inspectors, baggage handlers, and other security personnel may non-invasively inspect the contents of packages 22 for explosives, knives, guns, contraband, etc.

As will be described in greater detail below, the present invention is directed to an apparatus and method for reconstructing and displaying CT images with material differentiation based on atomic number, wherein the images are substantially free of beam hardening artifacts. Three exemplary algorithms for such reconstruction will be described, but one skilled in the art will appreciate that variants of the three exemplary algorithms are contemplated and considered within the scope of the claimed invention.

Figure 3:
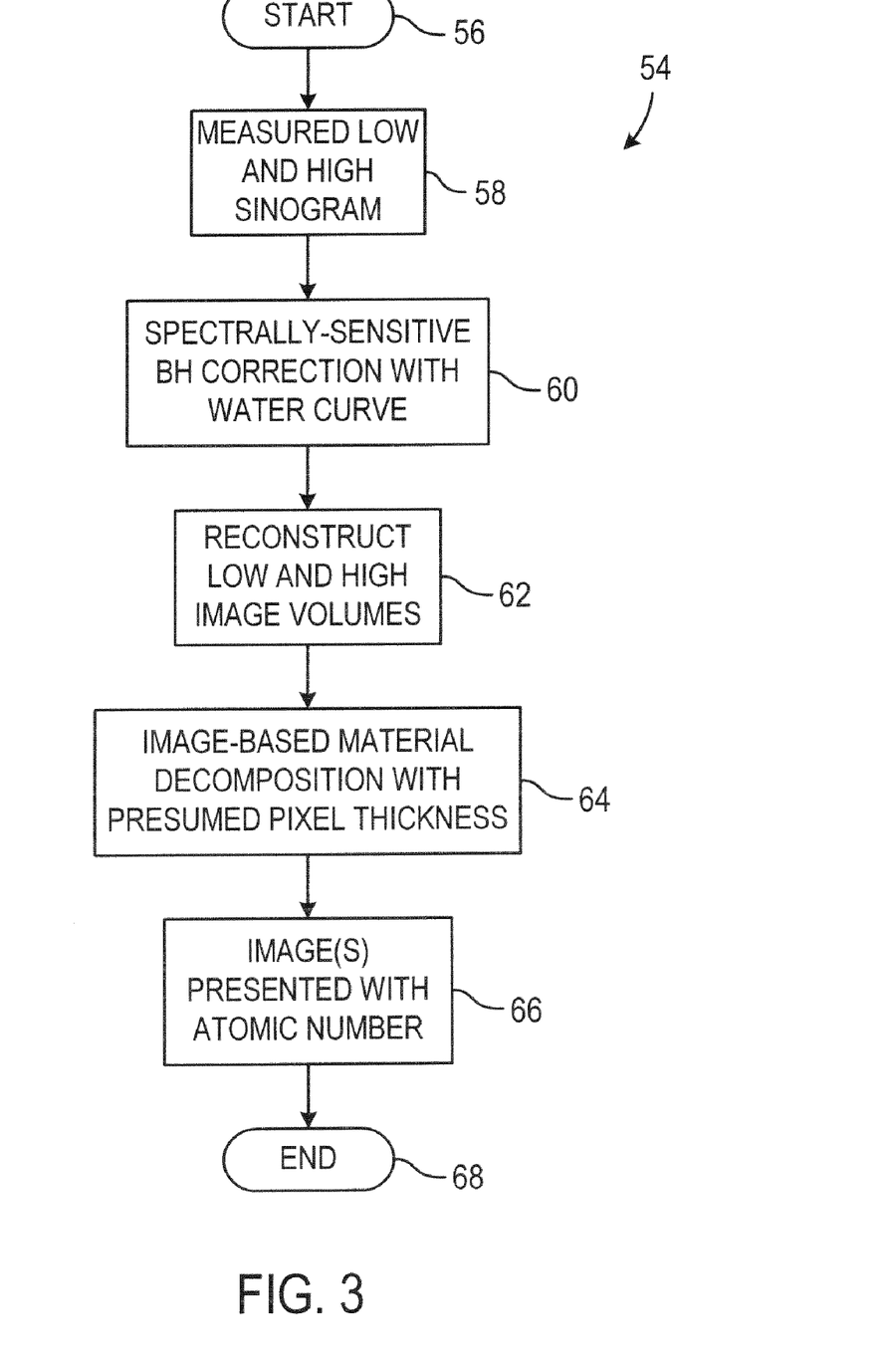
FIG. 3 is a flow chart setting forth the steps of an image-based material decomposition technique according to one aspect of the invention.

Referring now to FIG. 3, a flow chart for image-based atomic number mapping with pixel-by-pixel thickness according to one aspect of the present invention is shown. As will be explained below, the exemplary algorithm assumes a pixel thickness of 1.0 cm. One skilled in the art will appreciate that a "pixel" corresponds to a picture element of a reconstructed image. Thus, a presumed 1.0 cm thick pixel refers to the presumed thickness of the material imaged in each pixel. For algorithm 54, the material is presumed to be water.

Algorithm 54 begins at step 56 with the acquisition of a low energy sinogram and a high energy sinogram 58 in one of a number of dual-energy manners. In one preferred embodiment, the low energy sinogram is acquired in approximately one-half of a full gantry rotation plus detector fan-angle and the high energy sinogram in acquired in approximately one-half of a full gantry rotation plus detector fan-angle. In this regard, little over one full gantry rotation of data acquisition is segmented into a low energy half and a high energy half. This allows for nearly full 360 degree plus twice the fan angle acquisition without increasing scan time.

For step-and-shoot scanning, the linear motion is suspended during the acquisition of both kvp data sets corresponding to gantry rotation of one-full rotation plus twice the fan angle. Upon completion of this acquisition, the object is moved one detector width. For helical mode scanning, the gantry rotation and linear motion of the object are continuous constant values. The switching of kvp will occur periodically at the points where a complete set of helical data is acquired for each kvp. For example, for a pitch one-half helical scan, during every rotation of the gantry, the object will increment by one-half the width of the detector and the kvp is changed when the system reaches top-dead-center on every rotation. For a gated acquisition, the data and linear motion are adjusted to optimally match biological signatures, such as respiration and heart beat motion.

It is recognized that a number of techniques may be used to acquire the sinograms 58. For example, the x-ray tube may be alternately biased between a high kvp and a low kvp. or, a dynamic x-ray filter may be controlled such that the x-ray beam attenuated by the object to be imaged is cycled between high energy and low energy. It is also contemplated that a combination of x-ray tube and x-ray filter control may be used to acquire sinograms at different energy levels. Other dual-energy techniques are also contemplated, i.e., tube current control in conjunction with x-ray filter control. At 60, the sinograms undergo spectrally-sensitive beam hardening correction and cone beam correction to preserve the spectral information contained in each sinogram. Following beam hardening correction 60, the sinograms are reconstructed to form a low energy image and a high energy image in a conventional manner 62. It is typical for a properly calibrated CT system to produce registered low and high images by reconstruction even if the sinogram data is not registered.

The data for each pixel in the low and high energy images are then combined in an imaged-based material decomposition algorithm with a presumed pixel thickness at 64 to derive atomic number information for each pixel of the images. In other words, an atomic number map is generated for each image on a pixel-by-pixel basis. As will be described below, the atomic map information is used to determine the material imaged in each pixel of the images. The high and low energy images are then combined with the atomic number map to form a composite image 66 that is presented with both density and atomic number information. For example, it is contemplated that color-coding, shading, and the like of the usual CT gray-scale image may be used to differentiate materials in the composite image. The composite image is displayed and/or stored in a conventional scanner at 68 whereupon the process ends.

Figure 4:
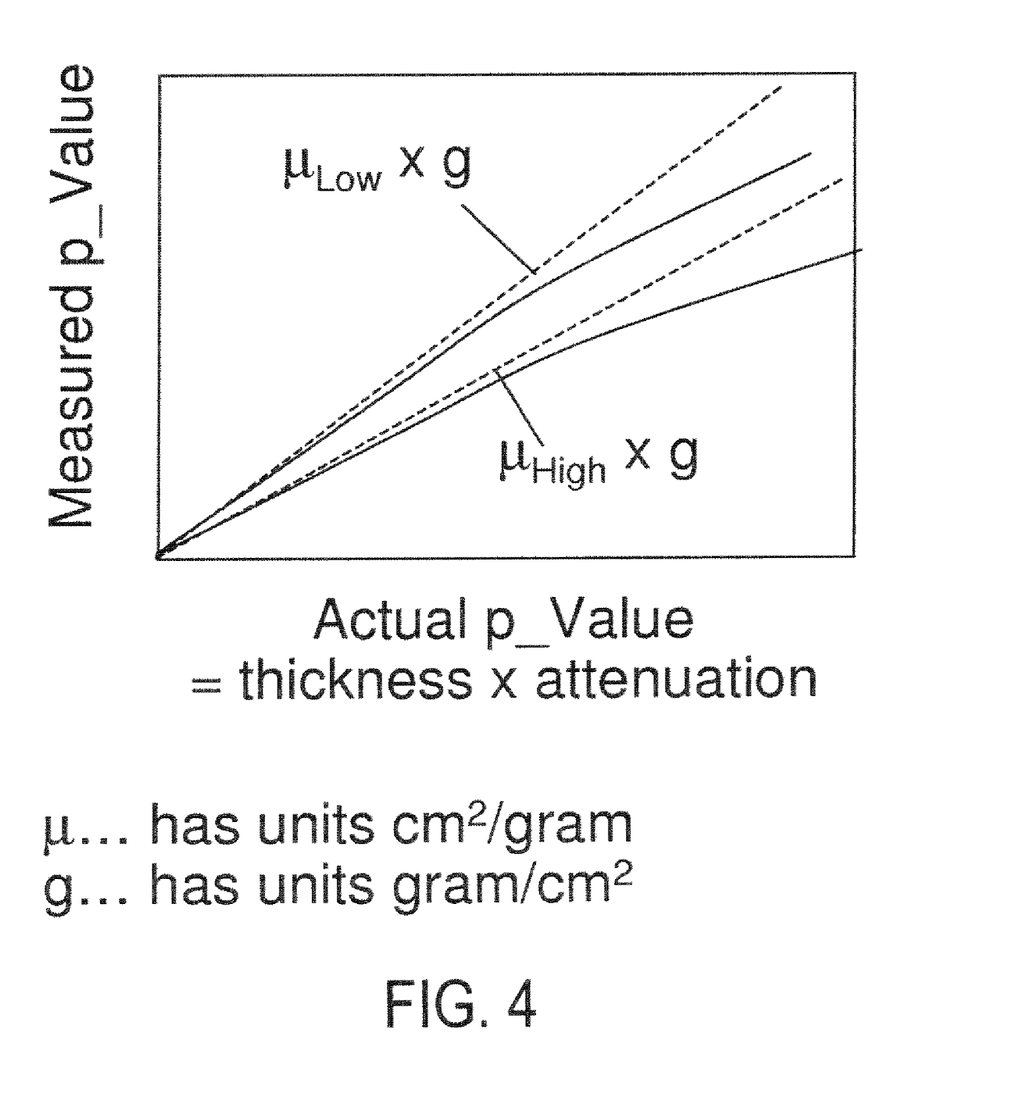
FIG. 4 is a graph illustrating measured $\rho$ values versus actual $\rho$ values for high kvp data and low kvp data.

As reference above, the high and low energy images are decomposed to determine atomic number information therefrom. This atomic number information is ascertainable because there is a different and unique relationship between measured $\rho$ values and actual $\rho$ values for each energy. This is illustrated in the graph of FIG. 4. Moreover, the relationship between measured and actual $\rho$ values will differ significantly depending upon the material through which the x-rays are attenuated. For the algorithm illustrated in FIG. 3, it has been presumed that the material that attenuates the x-rays is water. In this regard, the beam hardening correction preserves the spatial sensitivity information of the images by basing the correction on the linear extrapolation from the attenuation through 1.0 cm of water. Conventional beam hardening correction techniques use a linear relationship between measured and actual $\rho$ values with a fixed slope of 0.2 cm$^{-1}$ regardless of the spectral content. By taking the actual spectral content into consideration during beam hardening correction, the present invention has shown to reconstruct images with improved image quality.

The reconstruction technique described with respect to FIG. 3, for purposes of explanation, is referred to as a "first pass" beam hardening correction technique. However, this first pass technique may not to be optimal when a material other than water is presumed to be the material through which x-rays are attenuated. Accordingly, a "multi-pass" technique is shown in FIG. 5.

The "multi-pass" technique 70 is similar to the technique of FIG. 3 in that the imaging process begins at step 72 with the acquisition of a low energy sinogram and a high energy sinogram 74. The low and high energy sinograms undergo beam hardening correction at 76 followed by reconstruction of beam-hardening corrected, Hounsfield unit, low energy and high energy images 78. The beam hardening correction carried out at step 76 is similar to the beam hardening correction described above with respect to FIGS. 3 and 4. Specifically, for the first pass of beam hardening correction, it is presumed that water is the material that attenuates the x-ray beam.

The reconstructed beam-hardening corrected images are reprojected at 80 to obtain low and high energy sinograms with registration to the measured sinogram acquired at 74. In this regard, the images are reprojected twice, each time to register with either the low or high energy measured sinogram. The reprojection is preferably carried out with a courser matrix size to expedite execution of the algorithm. Following reprojection, material decomposition is performed on the re-projected sinograms at 82 to extract atomic number information for each ray of the registered sinograms. Thereafter, spectrally-sensitive beam hardening correction is carried out on the registered sinograms, but now using the atomic number information for each ray. The corrected sinograms are then reconstructed at 86 to yield low and high energy images. The images are then decomposed at 88 in a manner similar to that described with respect to FIG. 3. The low and high energy images are then registered and presented at 90 with atomic number information. The process then ends at 92.

Figure 5:
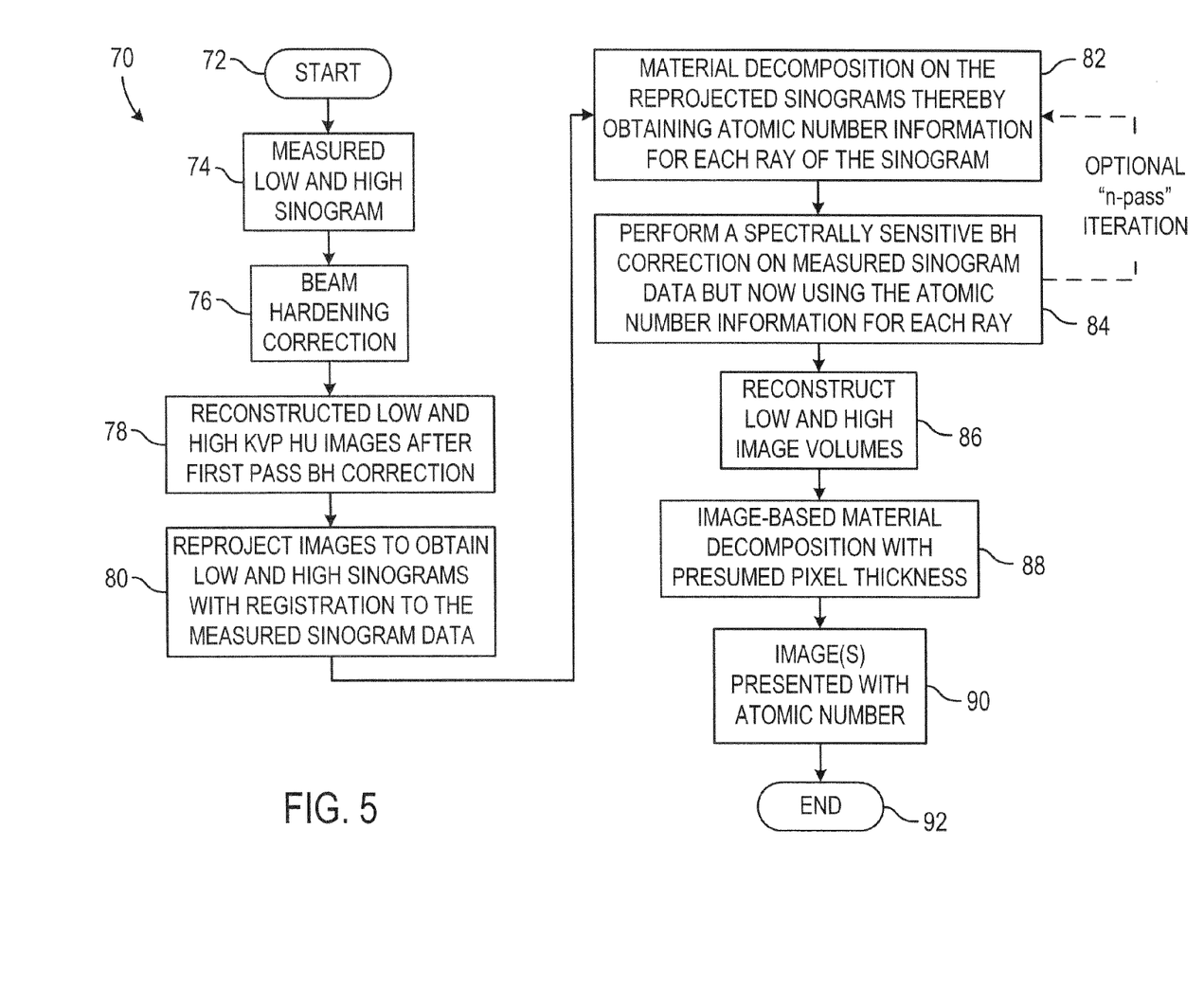
FIG. 5 is a flow chart setting forth the steps of an image-based material decomposition technique with multi-pass beam hardening correction according to another aspect of the invention.

While the algorithm of FIG. 5 has been described with respect to "two" beam hardening passes, it is contemplated that more than two passes or iterations may be carried out. In this regard, the spectrally-sensitive beam hardening corrected sinograms may be decomposed at 82 to re-determine atomic number information. In this regard, steps 82 through 84 may be iteratively repeated a desired number of times to improve the accuracy of the atomic number information. However, it is believed that two passes will be sufficient for most CT studies. For example, testing has shown that water and aluminum of a phantom can be correctly assigned an atomic number with two passes. Furthermore, those skilled in the art will appreciate that additional iterative reconstruction algorithms which effect a consecutive improvement in the atomic number information upon each iteration of the algorithm are contemplated.

Figure 6:
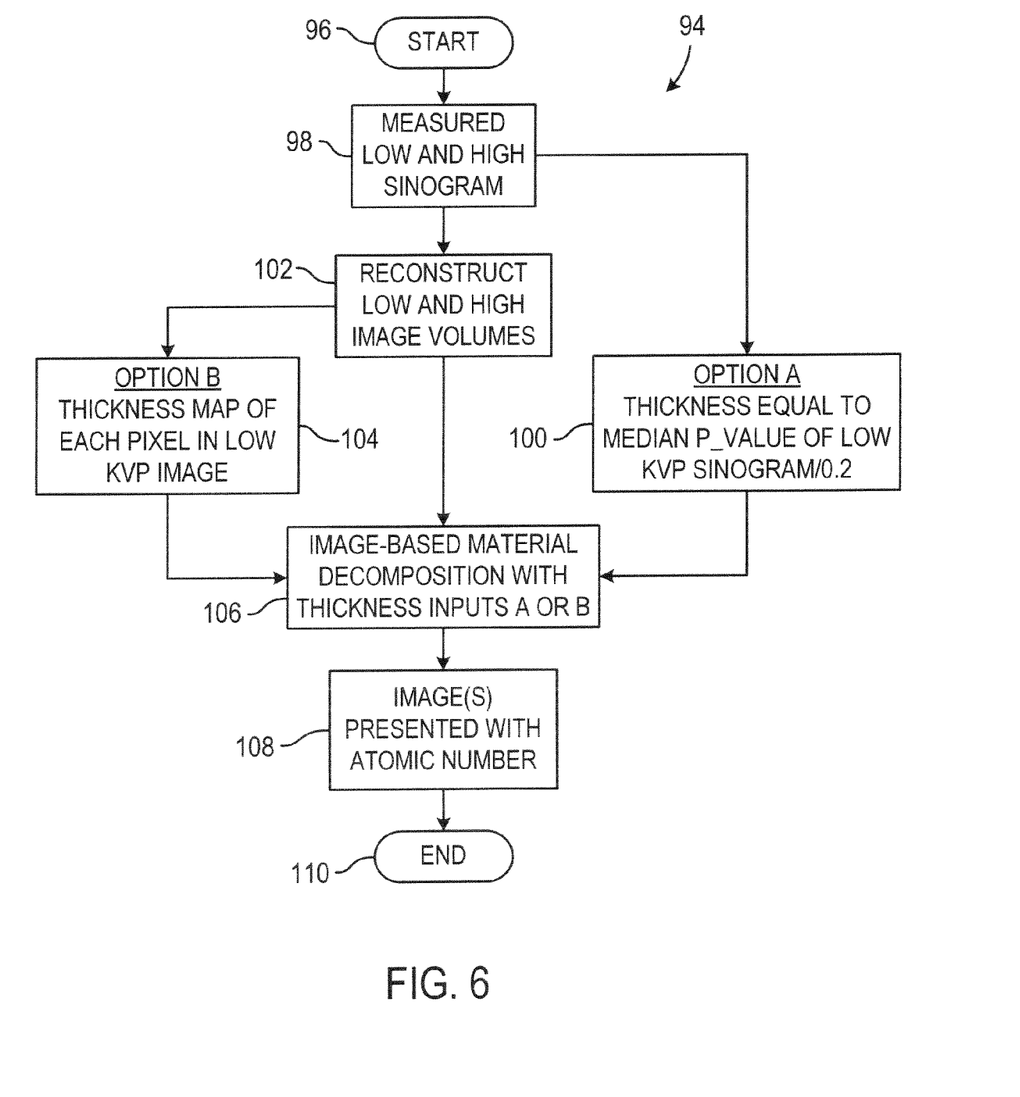
FIG. 6 is a flow chart setting forth the steps of another image-based material decomposition technique in accordance with the present invention.

Referring now to FIG. 6, another exemplary algorithm for image-based material decomposition with beam hardening correction is shown in flow chart form. Algorithm 94 is similar to the algorithm described with respect to FIG. 3, but does not include beam hardening correction of sinogram data before image reconstruction. Moreover, algorithm 94 avoids the reprojection step of the algorithm of FIG. 5. Thus, the imaging process 94 begins at 96 with the acquisition of low and high energy data 98. As referenced above, beam hardening correction is not performed prior to image reconstruction. In this regard, beam hardening artifacts are mitigated by the selection of a material thickness on a per-pixel basis.

Two techniques for determining material thickness are contemplated. In either approach, the low and high energy sinograms are reconstructed into low and high energy images 102. In one technique, the material thickness for each image pixel is set to the same value give by the median $\rho$ value of the low energy sinogram divided by a scalar 100, e.g., 0.2. In another technique, a separate thickness value is generated of each pixel in the low energy image 104. The thickness value is constructed by reprojection of each image pixel onto a trajectory along the low energy sinogram and selecting the median or maximum value of $\rho$ value on that trajectory divided by a scalar, e.g., 0.2. The trajectory can be pre-computed and available as a lookup table for every data set. In either approach 100 or 104, imaged-based material decomposition is performed 106 on the reconstructed low and high energy images using either a constant value for all pixels, formed by the median $\rho$ value of the low energy sinogram divided by a scalar as the material thickness value, or using a respective thickness value for each pixel. Following decomposition, the low and high energy images are registered and presented as a composite image with atomic number information differentiation at 108. The imaging process then ends at 110.

As described for each of the exemplary decomposition techniques, atomic number information is determined, in part, from information relating to the thickness of a material captured in a given image pixel. Specifically, attenuation due to thickness T of material M is equivalent to attenuation of material with interpolated atomic number Z and same thickness T. As such, the linear attenuation constant, $\alpha$, for a material illuminated with a broad spectrum of x-rays can be obtained as the sum with spectral weighting of the attenuation factor through a thickness T at each photon energy indexed by n. The spectral weighing $w_{bin,n}$ will be equal to the energy multiplied by the number of photons absorbed in the detector at the energy for energy-integrating detectors. Specifically:

$$\alpha_{bin} = \frac{-1}{T} \ln\left( \sum_{n} w_{bin,n} e^{-T\alpha_{Z,n}} \right), \quad \text{(Eqn. 1)}$$

where:

$w_{bin,n}$ is the energy weighting function for each bin at energy $E_n$, $\alpha_{Z,n}$ is the linear attenuation constant of element Z with density 1 g/cc at energy $E_n$.

Figure 7:
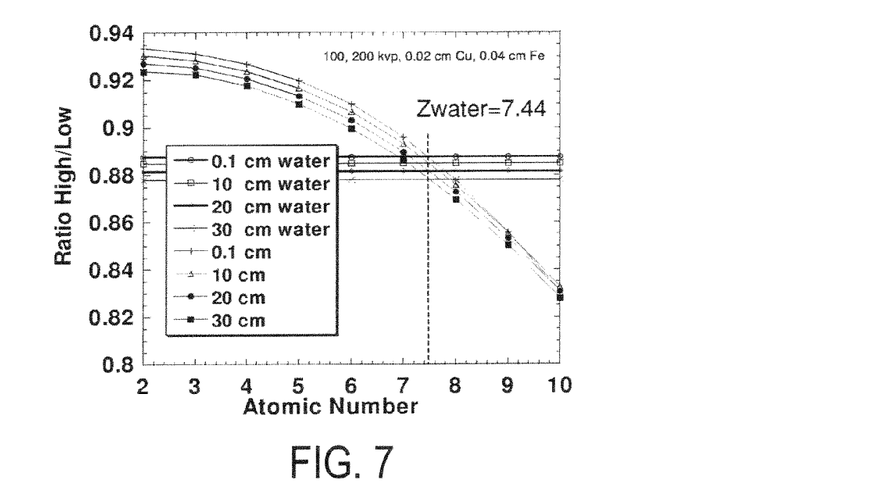
FIG. 7 is a graph illustrating a relationship between linear coefficient ratios and atomic number.

With this equation and knowledge about the spectral content of the two energy bins, it is possible to calculate and plot a ratio of high linear coefficient to low linear attenuation coefficients as a function of atomic number, as illustrated in FIG. 7. As shown, the ratio of linear coefficients can be plotted for each atomic element and thickness. The plot can be interpolated to extract the atomic number of any material M with thickness T. Accordingly, on a pixel-by-pixel basis for the high and low energy images reconstructed as described above, a linear coefficient ratio is determined. By interpolating the plot shown in FIG. 7, the atomic number for each pixel can be ascertained and used to differentiate materials in a composite image of the high and low energy images. The plot shown in FIG. 7 is preferably stored as a lookup table in computer readable memory of the CT scanner.

Figure 8:
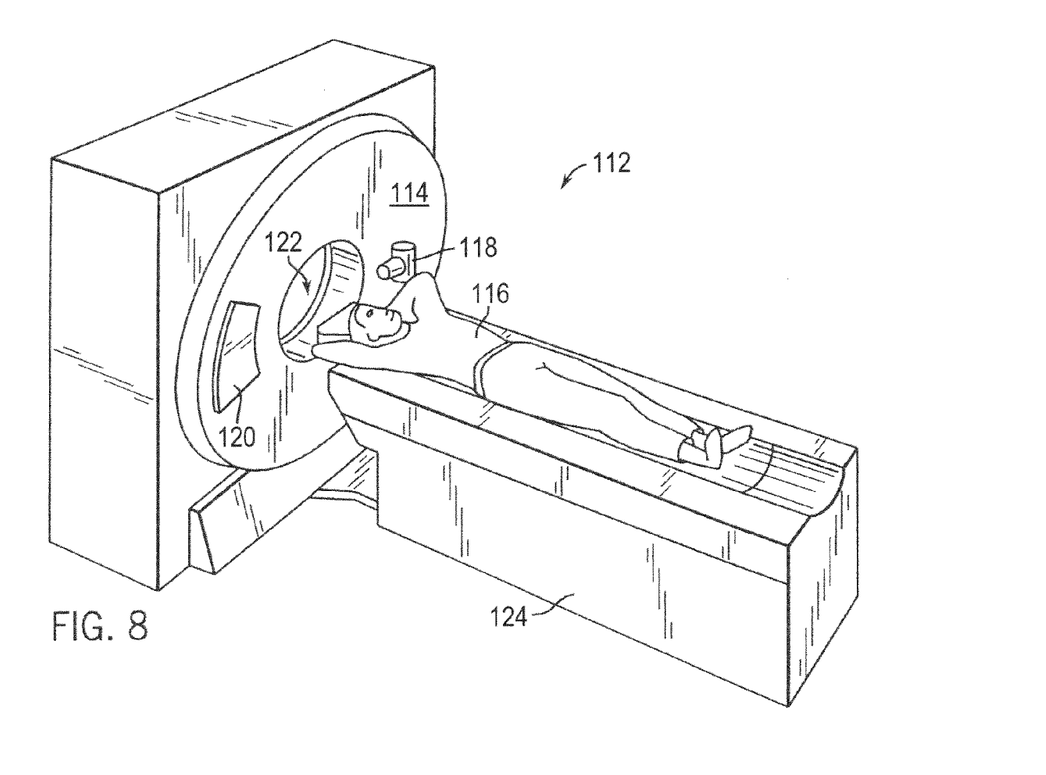
FIG. 8 is a pictorial view of a CT system for medical imaging.

The present invention is also applicable with a CT scanner for medical scanning. An exemplary medical CT scanner 112 is shown in FIG. 8. The scanner includes a gantry 114 housing an x-ray source 118 that projects a beam of x-rays toward a detector array 120 on the opposite side of the gantry 114. Detector array 120 senses the projected x-rays that pass through the patient 116. The patient is translated through gantry opening 122 in either a continuous or incremental manner by table 124. While a "third generation" CT scanner has been shown, the invention is applicable with other configured CT scanners including but not limited to "first", "second", "fourth", "fifth", "sixth", etc. generation systems.

Therefore, in accordance with one embodiment, the invention includes an imaging apparatus having a data acquisition system configured to reconstruct an image of an object. The apparatus further includes a computer programmed to define a given projection into a first segment and a second segment different from the first segment and acquire a first set of data in the first segment and acquire a second set of data in the second segment. The first set of data is acquired at a first energy level and the second set of data is acquired at a second energy level that is different from the first energy level. The computer is further programmed to reconstruct a first image from the first set of data and a second image from the second set of data, and then automatically register the first and the second images into a composite image substantially free of beam hardening artifacts and that at least provides material decomposition information.

In accordance with another embodiment, the invention includes a computer readable storage medium having a computer program stored thereon and representing a set of instructions that when executed by a computer causes the computer to perform image-based atomic number mapping of an object imaged in a dual-energy mode.

According to another embodiment, the invention is embodied in a method of CT imaging that includes determining a first attenuation coefficient for a given pixel in a first image and determining a second attenuation coefficient, different from the first attenuation coefficient, for the given pixel in a second image, different from the first image. The method further determines a linear coefficient ratio between the first attenuation coefficient and the second attenuation coefficient and determines an atomic make-up for the given pixel from the linear coefficient ratio. The method further includes the step of displaying a registered image comprised of the first and the second images with the given pixel in the registered image displayed in a conspicuous manner to indicate the atomic make-up of that imaged in the given pixel.

The present invention has been described in terms of the preferred embodiment, and it is recognized that equivalents, alternatives, and modifications, aside from those expressly stated, are possible and within the scope of the appending claims.

What is claimed is:

1. An imaging apparatus having a data acquisition system configured to reconstruct an image of an object and comprising a computer programmed to:
    define a given projection into a first segment and a second segment different from the first segment;
    acquire a first set of data in the first segment and acquire a second set of data in the second segment, wherein the first set of data is acquired at a first energy level and the second set of data is acquired at a second energy level that is different from the first energy level;
    reconstruct a first image from the first set of data and a second image from the second set of data;
    re-project the first image to a first set of corrected sinograms and re-project the second image to a second set of corrected sinograms;
    decompose the first and second sets of corrected sinograms and determine atomic number information for each ray of each corrected sinogram, wherein the step of decomposing comprises generating an atomic number of material composition map from the decomposition;
    reconstruct a first corrected image and a second corrected image from the first and the second sets of corrected sinograms; and
    automatically register the first and the second corrected images into a composite image substantially free of beam hardening artifacts, wherein the composite image provides material decomposition information.

2. The apparatus of claim 1 further comprising an x-ray energy source designed to emit an x-ray beam toward an x-ray detector spaced from the x-ray source by at least an object to be imaged, and wherein the first set of data is acquired with the x-ray source biased to a first voltage and the second set of data is acquired with the x-ray source biased to a second voltage different from the first voltage.

3. The apparatus of claim 2 wherein the second voltage is considerably less than the first voltage.

4. The apparatus of claim 1 wherein the computer is further programmed to correct the first and the second images for cone beam distortions prior to registration.

5. The apparatus of claim 1 wherein the computer is further programmed to perform spectrally-sensitive beam hardening correction, with a water curve, on the first set and the second set of data to yield a first sinogram and a second sinogram, respectively.

6. The apparatus of claim 5 wherein the computer is further programmed to reconstruct the first image from the first sinogram and reconstruct the second image from the second sinogram, and display the composite image with material differentiation by color-coding image pixels corresponding to various imaged materials.

7. The apparatus of claim 1 further comprising an x-ray source and an x-ray filter, and wherein the computer is further programmed to automatically control at least one of x-ray source energization and x-ray filter filtering to generate the first energy level and the second energy level.

8. The apparatus of claim 7 wherein the x-ray source is a single anode x-ray source.

9. The apparatus of claim 1 wherein the computer is further programmed to determine material composition of the composite image based on atomic numbers of that imaged in the composite image, the determination of the material composition achieved by:
    determining a first attenuation coefficient for a given pixel in the first image and a second attenuation coefficient for the given pixel in the second image;
    determining a ratio between the first attenuation coefficient and the second attenuation coefficient; and
    determining an atomic number for the given pixel in the composite image from the ratio.

10. The apparatus of claim 9 further comprising a computer readable storage medium having a look-up table stored thereon, and wherein the computer is further programmed to compare the determined ratio to the look-up table to determine the atomic number for the given pixel.

11. The apparatus of claim 1 wherein the first set of data includes a first sinogram and the second set of data includes a second sinogram, and wherein the computer is further programmed to:
    reconstruct the first image from the first sinogram and reconstruct the second image from the second sinogram with a first beam hardening correction;
    re-project the first image to a first set of corrected sinograms and re-project the second image to a second set of corrected sinograms;

decompose the first and the second sets of corrected sinograms and determine atomic number information for each ray of each corrected sinogram;

perform spectrally sensitive beam hardening correction, with the atomic number information, on the first and the second set of corrected sinograms;

reconstruct a first corrected image and a second corrected image from the spectrally sensitive beam hardening corrected sinograms;

register the first corrected image and the second corrected image to form a corrected composite image; and display with the corrected composite image with atomic number information differentiated in the corrected composite image.

12. The apparatus of claim 1 wherein the first set of data includes a first sinogram and the second set of data includes a second sinogram, and wherein the computer is further programmed to:

determine median ρ-value of second sinogram;

set baseline thickness to the median ρ-value;

iteratively determine a first attenuation coefficient for each pixel in the first image and a second attenuation coefficient for each pixel in the second image;

determine a ratio between the first attenuation coefficient and the second attenuation coefficient for each pixel;

determine an atomic number for each pixel in the composite image from a linear attenuation coefficient curve that is defined in the x-axis by atomic number and defined in the y-axis by possible ratios.

13. The apparatus of claim 1 wherein the computer is further programmed to:

determine a thickness for each pixel of the second image;

iteratively determine a first attenuation coefficient for each pixel in the first image and a second attenuation coefficient for each pixel in the second image;

determine a ratio between the first attenuation coefficient and the second attenuation coefficient for each pixel;

determine an atomic number for each pixel in the composite image from a linear attenuation coefficient curve that is defined in the x-axis by atomic number and defined in the y-axis by possible ratios, wherein the thickness determined for each pixel mitigates beam hardening artifacts for the pixel.

14. The apparatus of claim 1 configured to acquire CT data of luggage, packages, or parcels.

15. The apparatus of claim 1 configured to acquire CT data from a medical patient.

16. The apparatus of claim 1 further comprising a rotatable gantry defining a bore to receive an object for imaging, the gantry housing an x-ray source and an x-ray detector assembly that are rotated about the object during CT data acquisition, and wherein one projection of data is acquired in one gantry rotation plus twice a detector fan-angle, and wherein the first segment is defined by one-half of gantry rotation plus a fan-angle and the second segment is defined by the other one-half of gantry rotation plus a fan-angle.

17. The apparatus of claim 16 wherein the computer is further programmed to coordinate gantry rotation with linear motion of the object to effect a helical scan, and wherein periodic switching of kvp corresponds to linear motion of one-half of detector width.

18. The apparatus of claim 16 wherein the computer is further programmed to coordinate gantry rotation with linear motion of the object to effect a step-and-shoot scan, and wherein the linear motion is suspended during acquisition of one projection data corresponding to two segments and linear advancement between acquisitions.

19. A computer readable storage medium having a computer program stored thereon and representing a set of instructions that when executed by a computer causes the computer to perform image-based atomic number mapping of an object imaged in a dual-energy mode, wherein the set of instructions comprise:

defining a given projection into a first segment and a second segment different from the first segment;

acquiring a first set of data in the first segment and acquiring a second set of data in the second segment, wherein the first set of data is acquired at a first energy level and the second set of data is acquired at a second energy level that is different from the first energy level;

reconstructing a first image from the first set of data and a second image from the second set of data;

re-projecting the first image to a first set of corrected sinograms and re-projecting the second image to a second set of corrected sinograms;

decomposing the first and second sets of corrected sinograms and determining atomic number information for each ray of each corrected sinogram, wherein the step of decomposing comprises generating an atomic number of material composition map from the decomposition;

reconstructing a first corrected image and a second corrected image from the first and the second sets of corrected sinograms; and automatically registering the first and the second corrected images into a composite image substantially free of beam hardening artifacts, wherein the composite image provides material decomposition information.

20. The computer readable storage medium of claim 19 wherein the computer is further caused to:

automatically register a high kvp image and a low kvp image to form a composite image;

associate an atomic number of reach pixel of the composite image; and color-code the composite image to differentiate imaged materials from one another based on atomic number.

21. The computer readable storage medium of claim 20 wherein the computer is further caused to iteratively determine the atomic number for each pixel of the composite image based on a linear coefficient curve.

22. A method of CT imaging comprising the steps of:

determining a thickness for each pixel;

determining a first attenuation coefficient for a given pixel in a first image;

determining a second attenuation coefficient, different from the first attenuation coefficient, for the given pixel in a second image, different from the first image;

determining a linear coefficient ratio between the first attenuation coefficient and the second attenuation coefficient;

determining an atomic make-up for the given pixel from the linear coefficient ratio, wherein the thickness determined for each pixel mitigates beam hardening artifacts for the pixel; and displaying a registered image comprised of the first and the second images with the given pixel in the registered image displayed in a conspicuous manner to indicate the atomic make-up of that imaged in the given pixel.

23. The method of claim 22 wherein the first image is acquired at a first energy level and the second image is acquired at a second energy level, different from the first energy level.

24. The method of claim 23 further comprising the step of alternating an x-ray source between a high kvp and a low kvp to acquire the first and the second images, respectively.

25. The method of claim 22 wherein the registered image is substantially free of beam hardening artifacts.

26. The method of claim 22 wherein the atomic make-up of that imaged in the given pixel is indicated by at least one of color-coding or shading.

* * * * *